United States Patent [19]

Jones et al.

[11] 4,229,478
[45] Oct. 21, 1980

[54] NAPHTHAQUINONE ANTI-PSORIATIC AGENTS

[75] Inventors: Gordon H. Jones, Cupertino; John Young, Redwood City, both of Calif.

[73] Assignee: Syntex (U.S.A.) Inc., Palo Alto, Calif.

[21] Appl. No.: 912,697

[22] Filed: Jun. 5, 1978

[51] Int. Cl.² .......................................... A61K 31/12
[52] U.S. Cl. ............................. 424/331; 260/396 R; 424/251; 424/263; 424/304; 424/311; 424/320
[58] Field of Search .................... 424/331; 260/396 R

[56] References Cited

U.S. PATENT DOCUMENTS 3,914,264  10/1975  Marsico et al. ................. 260/396 R

OTHER PUBLICATIONS

Chemical Abstracts 52:10211 (1958).

*Primary Examiner*—Leonard Schenkman

*Attorney, Agent, or Firm*—Tom M. Moran; Alan M. Krubiner

[57] ABSTRACT

Psoriasis in mammals is relieved by topically administering substituted naphthaquinones of the formula:

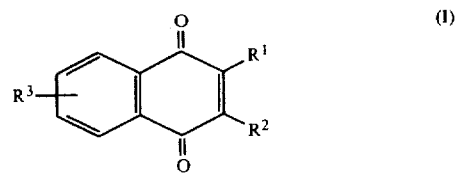

where $R^1$ and $R^2$ are the same or different and are hydrogen, hydroxy, alkoxy or acylamino and $R^3$ is hydrogen, halo, cyano or alkoxy with the proviso that $R^1$ and $R^2$ are not both hydrogen.

8 Claims, 4 Drawing Figures

FIG_1

FIG_2

10

11

12

12a R=H
 b R=CH₃CO-

13

13a R=H
 b R=CH₃CO-

14

14a R³= Cl
 b R³= CN
 c R³= PhS-
 d R = 
 e R³= 
 f R³= 
 g R³= 
 h R³=

14i R³= 
 j R³= 
 k R³= 
 l R³= 
 m R³=

14n R³= 
 o R³= 
 p R³= 
 q R³= MeS-
 r R³= PhCH₂S-
 s R³= nC₁₂H₂₃S-
 t R³= MeOOCCH₂S-
 u R³=

FIG_3a

FIG_3b

NAPHTHAQUINONE ANTI-PSORIATIC AGENTS

FIELD OF THE INVENTION

The invention relates to pharmaceutical compositions which are useful in inhibiting certain dermatological conditions. More particularly, this invention relates to pharmaceutical compositions and methods useful in relieving the effects of certain chronic recurrent papulosquamous dermatoses, e.g., psoriasis. This invention also includes a number of novel substituted naphthoquinones and methods for their preparation as well as intermediates useful in such preparation.

DESCRIPTION OF THE PRIOR ART

Psoriasis is a skin disease characterized in part by excessive proliferation of cells of the epidermis which remain strongly adherent and build up into a scaley plaque typical of the disease. Currently available therapies, which are not curative, depend on the control of epidermal cell proliferation through the use of hormonal agents, such as corticosteroids or through the use of compounds related to cancer chemotherapy such as hydroxyurea, methotrexate, and the nitrogen mustards.

While the above agents are effective to a certain extent, they cause numerous severe undesirable side effects including renal irritation and erythema.

SUMMARY

Certain naphthoquinone derivatives have now been shown to be effective in preventing epidermal cell proliferation when applied topically to animal skin. They also have been shown to be effective as anti-psoriatic agents in humans.

1,4-Naphthoquinones of the formula

(I)

where $R^1$ and $R^2$ are the same or different and are hydrogen, hydroxy, $C_1$ to $C_{18}$ linear or branched alkoxy or $C_2$ to $C_7$ linear or branched acylamino and $R^3$ is selected from the group hydrogen, halo, cyano, $C_1$ to $C_{18}$ linear or branched alkoxy and the group $-S(O)_nR$ where R is selected from the group $C_1$ to $C_{18}$ linear or branched alkyl optionally substituted with phenyl or substituted phenyl, the substituents selected from $C_1$ to $C_4$ linear or branched alkyl, $C_1$ to $C_4$ linear or branched alkoxy, halo and $C_2$ to $C_4$ linear or branched acyl, $C_2$ to $C_7$ linear or branched acyloxy, phenyl optionally substituted with halo, dihalo, cyano, nitro, amino, $C_2$ to $C_7$ linear or branched acylamino, di-$C_2$ to $C_7$ linear or branched acylamino, $C_1$ to $C_{18}$ linear or branched alkoxy or $C_1$ to $C_{18}$ linear or branched alkyl, heterocyclic aryl optionally substituted with halo, cyano, $C_1$ to $C_4$ linear or branched alkyl or $C_1$ to $C_4$ linear or branched alkoxy and the pharmaceutically acceptable salts of said heterocyclic aryl and n is the integer 0, 1 or 2, (II)

where $R^1$ and $R^2$ are defined above; or (III)

where $R^3$ is as previously defined with the proviso that $R^3$ is not hydrogen in the compound of formula (III) and that $R^1$ and $R^2$ are not both hydrogen in the compound of formula (I), have useful activity in mammals in that they display anti-psoriatic activity.

A survey of the prior art has revealed that some of the compounds of formula (I) are not novel. For example, the compound 6-bromo-2,3-dihydroxy-1,4-naphthoquinone has been reported by Weygand, German 859,008. While this compound is recognized as a valuable intermediate for the preparation of dyestuffs, no form of useful biological activity has been ascribed to it. Further, there has been no disclosure or suggestion in the prior art that such a compound is likely to possess any particular useful biological activity. Specifically, any suggestion that this compound might have anti-psoriatic activity has not been advanced.

Related naphthoquinones having antifungal and antibacterial activity can be found in U.S. Pat. No. 3,914,264 and West German Offenlegungsschrift Nos. 2,135,712, 2,456,655 and 2,520,739. However, none of these disclosures have recognized the use of these or related naphthoquinone compositions as anti-psoriatic agents.

Briefly, the objects of the present invention as hereinafter will become more readily apparent from the following description in connection with the accompanying drawings in which.

Accordingly, in its broadest aspect, the present invention provides a pharmaceutical composition having anti-psoriasis activity comprising a compound of the formula:

together with at least one pharmaceutically acceptable carrier wherein $R^1$ and $R^2$ are the same or different and are hydrogen, hydroxy, $C_1$ to $C_{18}$ linear or branched alkoxy or $C_2$ to $C_7$ linear or branched acylamino and $R^3$ is selected from the group hydrogen, halo, cyano, $C_1$ to $C_{18}$ linear or branched alkoxy and the group $-S(O)_nR$ where R is selected from the group $C_1$ to $C_{18}$ linear or branched alkyl optionally substituted with phenyl or substituted phenyl, the substituents selected from $C_1$ to $C_4$ linear or branched alkyl, $C_1$ to $C_4$ linear or branched alkoxy, halo and $C_2$ to $C_4$ linear or branched acyl, $C_2$ to $C_7$ linear or branched acyloxy, phenyl optionally substituted with halo, dihalo, cyano, nitro, amino, $C_2$ to $C_7$ linear or branched acylamino, di-$C_1$ to $C_{18}$ linear or branched acylamino, $C_1$ to $C_{18}$ linear or branched alkyl or $C_1$ to $C_{18}$ linear or branched alkoxy, heterocyclic aryl optionally substituted with halo, cyano, $C_1$ to $C_4$ linear or branched alkyl or $C_1$ to $C_4$ linear or branched alkoxy and the pharmaceutically acceptable salts of said heterocyclic aryl and n is the integer 0, 1 or 2;

where $R^1$ and $R^2$ are as previously defined; or where $R^3$ is as previously defined with the proviso that $R^3$ is not hydrogen in the compound of formula (III) and that $R^1$ and $R^2$ are not both hydrogen in the compound of formula (I), being adapted to topical applications in mammals.

Examples of $R^1$ and $R^2$ which may be present in the compounds of formulas (I) and (II) are hydrogen, hydroxy, methoxy, ethoxy, n-propoxy, iso-propoxy, n-butoxy, t-butoxy, 1-ethylpropoxy, neopentoxy, n-dodecyloxy, and the like. Examples of $R^3$ in the compounds of formula (I) or (III) are illustrated by bromo, chloro, fluoro, cyano, methylthio, phenylthio, methoxy, ethoxy, n-propoxy and the like.

Preferably, $R^1$ and $R^2$ are the same and are hydroxy, methoxy, ethoxy, n-butoxy, sec-butoxy and t-butoxy, particularly hydroxy. Where $R^1$ and $R^2$ are different, preferably $R^1$ is methoxy and $R^2$ is hydrogen.

Preferably the compounds of the present invention of formulas (I) and (II) have $R^3$ substituted at the 5- or 6-position of the naphthoquinone ring. The substituents preferably being bromo, chloro, fluoro, cyano, phenylthio, thiomethyl, methoxy, ethoxy, n-propoxy, iso-propoxy, n-butoxy, sec-butoxy, 5-butoxy, acetyl and benzoyl.

Particularly preferred are the following compounds:
2,3-dihydroxy-6-bromo-1,4-naphthoquinone;
2,3-dihydroxy-6-methoxy-1,4-naphthoquinone;
6-chloro-oxalin;
6-fluoro-oxalin;
6-bromo-oxalin;
6-methoxy-oxalin;
2,3-dihydroxy-5-chloro-1,4-naphthoquinone;
2,3-dihydroxy-6-chloro-1,4-naphthoquinone;
2,3-dihydroxy-6-fluoro-1,4-naphthoquinone;
2,3-dihydroxy-6-cyano-1,4-naphthoquinone;
2,3-dihydroxy-5-cyano-1,4-naphthoquinone;
2,3-dimethoxy-5-phenylthio-1,4-naphthoquinone;
2,3-dihydroxy-5-phenylthio-1,4-naphthoquinone; and
2-methoxy-1,4-naphthoquinone.

The compounds according to the present invention may be formulated for administration in any convenient way by analogy with other topical compositions and the invention therefore includes within its scope such pharmaceutical compositions comprising a compound of formulas (I), (II), (III) as mixtures thereof adapted for use in mammals. These compositions may be presented for use in any conventional manner with the aid of any of a wide variety of pharmaceutical carriers or vehicles.

Generally, the anti-psoriatic manifestation in mammals, particularly humans, is combatted by contacting the inflamed areas with a therapeutically effective amount of the naphthoquinone-containing compositions of this invention, that is, an amount which results in a lessening of the epidermal cell proliferation (an anti-psoriatic effect). Preferably the naphthoquinones are first formulated to prepare a suitable pharmaceutical formulation, as discussed hereinafter, which is then placed in contact with the afflicted area(s). An effective amount of the naphthoquinone will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to affect an anti-psoriatic response, but not enough to adversely effect the recipient, is applied to the afflicted area(s).

The naphthoquinones of this invention may be formulated with suitable pharmaceutical vehicles known in the art to form particularly effective topical compositions. As disclosed above, an effective amount of the naphthoquinone is about 0.001% w to about 10% w of the total formulated composition. The rest of the formulated composition will be about 90% w to about 99.999% w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed in small globules in another substance (e.g., a glycol-water solvent phase) which may be employed as the primary solvent for the naphthoquinones therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| | | |
|---|---|---|
| Water/glycol mixture (15% or more glycol) | 50-99 | parts by weight |
| Fatty Alcohol | 1-20 | |
| Non-ionic Surfactant | 0-10 | |
| Mineral Oil | 0-10 | |
| Typical Pharmaceutical Adjuvants | 0-5 | |
| Active Ingredients | 0.001-10 | |

The fatty alcohol, non-ionic surfactant, and other adjuvants are discussed in U.S. Pat. No. 3,934,013 to Poulsen which is incorporated herein by reference.

The naphthoquinones of this invention may also be formulated as topical ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | | |
|---|---|---|
| White Petrolatum | 40-94 | parts by weight |
| Mineral Oil | 5-20 | |
| Glycol Solvent | 1-15 | |
| Surfactant | 0-10 | |
| Stabilizer | 0-10 | |
| Active Ingredients | 0.001-10.0 | |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| | | |
|---|---|---|
| Active Ingredients | 0.001-10.0 | parts by weight |
| Propylene Carbonate | 1-10 | |
| Solvent | 1-10 | |
| Surfactant | 0-10 | |
| White Petrolatum | 70-97 | |

Suitable solvents, surfactants, stabilizers, etc. are discussed in U.S. Pat. No. 3,934,013 and such are incorporated herein by reference.

A suitable topical "non-classical" anhydrous, water washable "ointment type" base is described in U.S. Pat. No. 3,592,930 to Katz and Neiman, and that patent is incorporated herein by reference. A representative composition of this invention utilizing such base is as follows:

| | | |
|---|---|---|
| Glycol Solvent | 40-35 | parts by weight |
| Fatty Alcohol | 15-45 | |
| Compatible Plasticizer | 0-15 | |
| Compatible Coupling Agent | 0-15 | |
| Penetrant | 0-20 | |
| Active Ingredients | 0.001-10.0 | |

Figure 1:
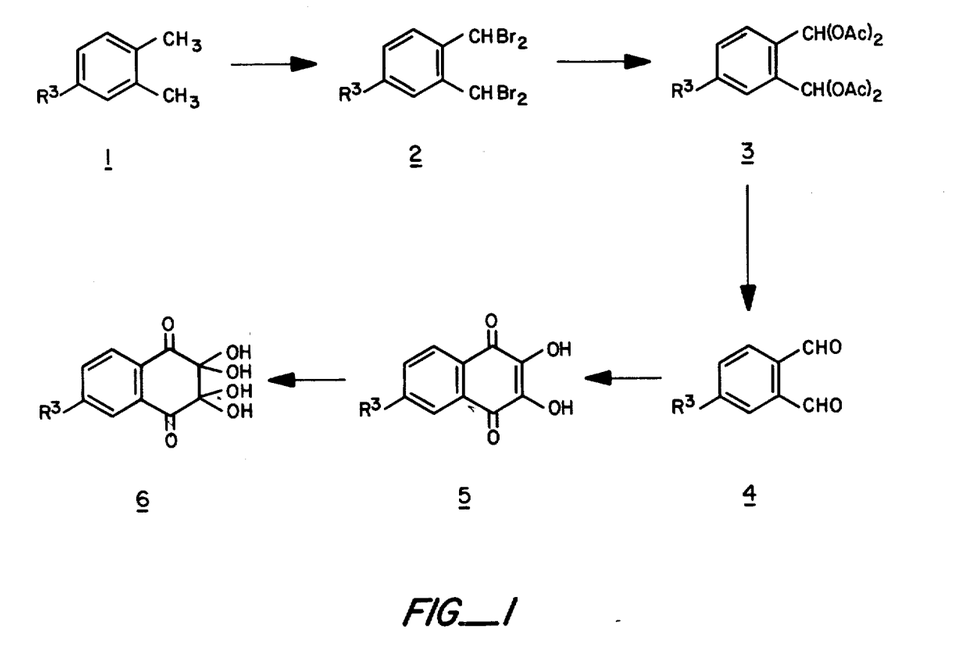
FIG. 1 is the reaction sequence for the preparation of the compounds of the present invention of formlula (III)

One aspect of the process for preparing the naphthoquinones of the present invention is disclosed in the aforesaid Weygand patent and illustrated by the reaction sequence of FIG. (I) for the preparation of 2,3-dihydroxy-6-substituted naphthoquinones, i.e., the compounds of formula (I) where $R^1=R^2=OH$ and $R^3$ is as previously defined.

Initially, the methyl groups of the $R^3$ substituted ortho-xylene (compounds 1) are directly halogenated. Disubstitution of halo on each of these groups is found to be most facil when bromo is the desired halo substituent. The reaction occurs readily using N-bromosuccinimide as the brominating agent. See for example, Djerassi, Chem. Revs., 43, 271 (1948). Compound(s) 2, the alpha, alpha, beta, beta-tetrabromo-ortho-xylene is next dehalogenated in a manner known for the hydrolysis of gem-dihalides in the presence of a suitable catalyst. The catalysts include, for example, calcium carbonate, sulfuric acid, morpholine and various silver salts. Typically a mixture of acetic acid, compound(s) 2 and silver acetate is heated, resulting in dehalogenating compound(s) 2 to compound(s) 3 which is readily converted to compound(s) 4 typically with base such as sodium bicarbonate. The 6-substituted-1,2-phthalaldehyde intermediate is next converted to the 6-substituted-2,3-dihydroxy-1,4-naphthoquinone compound(s) 5 the compounds of the present invention of formula (I) where $R^1=R^2=OH$, by reaction with glyoxal. This reaction is reported in some detail in the aforesaid Weygand reference.

Compound(s) 5 (i.e. the compound(s) of formula (I) where $R^1=R^2=OH$ and $R^3$ is as previously defined) when treated with a mixture of chlorine in acetic acid undergoes facile oxidation to produce optionally-6-substituted-1,2,3,4-tetrahydrotetraoxonaphthalene dihydrate, compound 6, i.e. the compounds of formula (I) where $R^1=R^2=$dihydroxy. The reaction is typically carried out by passing chlorine gas through a 50% aqueous acetic acid solution of compound(s) 5, at about 10° to about 100°, preferably 20° to 40° for a time sufficient to complete the reaction, typically 0.5 to 48 hours, isolating the oxidized compound(s) 6 by cooling the final reaction solution. The procedure is disclosed in detail in British Pat. No. 1,243,402. This procedure is also effectively employed to produce compound(s) 6 by using 6-substituted-2,3-dialkoxy-1,4-naphthoquinones, i.e., where $R^1$ is the same or different than $R^2$ and is $C_1$ to $C_{18}$ linear or branched alkoxy. Other effective oxidizing agents include alkali metal persulfates, hydrogen peroxide, sodium peroxide, bromine in acetic acid and the like. Temperatures and times of reaction for these other oxidizing agents are well known by those skilled in the art. It is sometimes more convenient to prepare the above disclosed 6-substituted-1,2-phthalaldehyde compound(s) 4 directly from compound(s) 1 by the classical Etard oxidation. See for example Hartford et al, Chem. Revs., 58, 1 (1958). This oxidation is readily effected with chromyl chloride.

The compounds of the present invention of formula (I) bearing the 6- or the 5-substituent, particularly the 5-substituent may also be prepared starting with a 2,3-dihalonaphthoquinone, preferably 2,3-dichloro-1,4-naphthoquinone (FIG. 2, compound 7) and directly nitrating. The reaction proceeds in the manner known for polycyclic aromatic compounds to yield a mixture of the 5- and 6-nitro-2,3-dichloro-1,4-naphthoquinones (compounds 8 and 9). The reaction is conducted typically with concentrated nitric acid in a low pH solvent medium, preferably concentrated sulfuric acid, typically at 20° to 100° for a time sufficient to complete the reaction. Depending on the reaction temperature and times of reaction, ratios of the 5-nitro isomer:6-nitro isomer mixture may range from 10:1 to 1:10, typically 8:1.

Compounds of the present invention of formula (I) where $R^1=R^2=$alkoxy (FIG. 3a, compounds 10 and 11) are synthesized from compounds 8 and 9 by condensing them with an alkali metal compound, such substituted with the desired alkoxide moiety. The reaction is preferably conducted in an inert organic solvent such as tetrahydrofuran, dimethylsulfoxide, dimethylformamide and the like at temperatures from about 20° to about 100° for a time sufficient to assure completeness of reaction, i.e., for about 2 hours to about 48 hours.

The compounds of this invention of formula (I) where $R^1=R^2=$alkoxy and $R^3$ is 5- or 6-amino (FIG. 3a, compounds 12a and 13a) are prepared from compounds 10 and 11 by catalytic or non-catalytic reduction processes known in the prior art. Metal-acid reducing agent compositions, such as granulated iron and hydrochloric acid, tin and hydrochloric acid, and the like or neutral reducing agent compositions such as zinc dust and aqueous alcohol or aluminum amalgam and aqueous alcohol as well as organometallic reducing agents such as lithium aluminum hydride, sodium borohydride and the like may be used in this reduction. Preferably, the reduction is accomplished by treating the compounds 10 and 11 with excess hydrazine in the presence of a catalytically sufficient amount of palladium, typically on carbon. The reaction readily occurs at room temperature, the time of reaction being governed by the rate of addition of the hydrazine to the reaction mixture such typically being about 1 to about 10 hours.

Figure 3A:
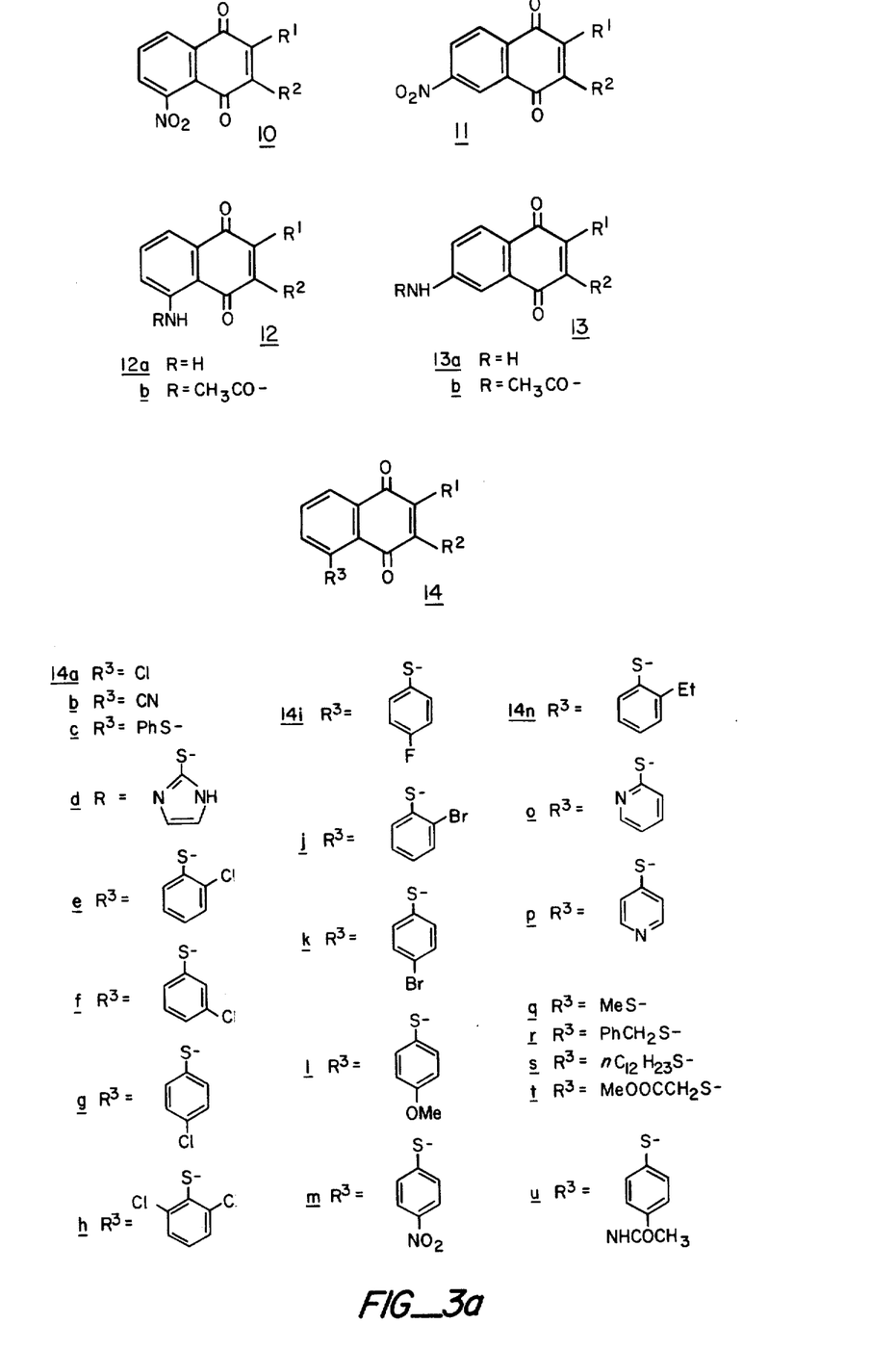
FIGS. 3a and 3b are illustrative compounds of the present invention of formulas (I) and (II).

Compounds 12a and 13a are converted to the desired aryl or alkylamides by reaction with the corresponding aryl or alkyl acid chlorides, acid anhydrides or carboxylic acids or to the desired alkylamines by reaction with the corresponding alkyl halides. For example, in the preparation of the 5-acetamido-2,3-dimethoxy-1,4-naphthoquinone, a solution or dispersion of compound(s) 12a is first made in an inert organic solvent such as chloroform, methylene chloride, and the like having present an acid acceptor such as pyridine. Excess acetyl chloride is added at $-10°$ to 75°, preferably 20°, the reaction being complete after about 30 minutes. The 5- or 6-(N-alkyl or N,N-dialkylamino)-1,4-naphthoquinones are typically prepared by heating the corresponding alkyl halide in a stoichiometric amount with the compounds 12a or 13a at 30° to about 100° for a time sufficient to complete the reaction, i.e., 30 minutes to 24 hours.

The compounds of the present invention 12a and 13a also serve as intermediates for a number of other compounds of the present invention such bearing substitution at 5- or 6-position of the 1,4-naphthoquinone nucleus. These compounds are converted into the compounds of the present invention where $R^3$ is halo (compounds 14a for example) by adding to the compound 12a in an acidified aqueous solution, a solution of an alkali metal nitrite. This initial reaction forms the diazonium salt at the 5- or 6-position of the naphthoquinone ring. The salt is decomposed with a solution of cuprous halide dispersed or dissolved in the corresponding halogen acid (the Sandmeyer reaction). This classical reaction is treated extensively in Bigelow, Org. Synthesis, Coll. Vol. I, 126-133 (1941).

A modification of the above Sandmeyer reaction is useful in the preparation of the compounds of the present invention of formula (I) where $R^3$ is cyano (compound 14b) in that the diazonium salt, rather than being decomposed in the presence of cuprous halide/halogen acid is decomposed in the presence of an alkali metal cyanide and a cuprous halide. See Clarke and Read, Org. Synthesis, Coll. Vol. I, 514 (1941) for a further explanation of the considerations involved in this modified Sandmeyer reaction.

The compounds of the present invention where $R^3$ is a thiol-substituted heterocyclic aryl compound optionally substituted with at least one substituent selected from the group halo, cyano, $C_1$ to $C_4$ linear or branched alkyl and $C_1$ to $C_4$ linear or branched alkoxy (compounds 14c-14p and 14u) or alkylthio (compounds 14q-14t) may also be prepared from the diazonium salt (above). For example, the diazonium salt of compound 12a (FIG. 3a) is reacted with an alkali solution of thiophenol to yield the compounds of the present invention of formula (I) where $R^3$ is 5-phenylthio (FIG. 3a, 14c). Typically, the displacement reaction of the diazonium salt is carried out at 30°-75° adding an alkali solution of the thiol-substituted heterocyclic aryl compound in an inert organic solvent. Solvents of preference are the inert solvents such as ethylacetate, tetrahydrofuran and the like. Reaction times may vary from 10 minutes to about 24 hours. The 5-aryl compounds are preferably prepared by adding the 2,3-dialkoxy-5-nitro-1,4-naphthoquinone (FIG. 3a, compound 10a) to a solution of the thiol-substituted heterocyclic aryl compound admixed with an alkali metal hydride in an inert organic solvent such as dimethylformamide. The reaction is typically conducted at $-75°$ to $-25°$ C. over a period of about 10 to about 60 minutes.

Figure 3B:
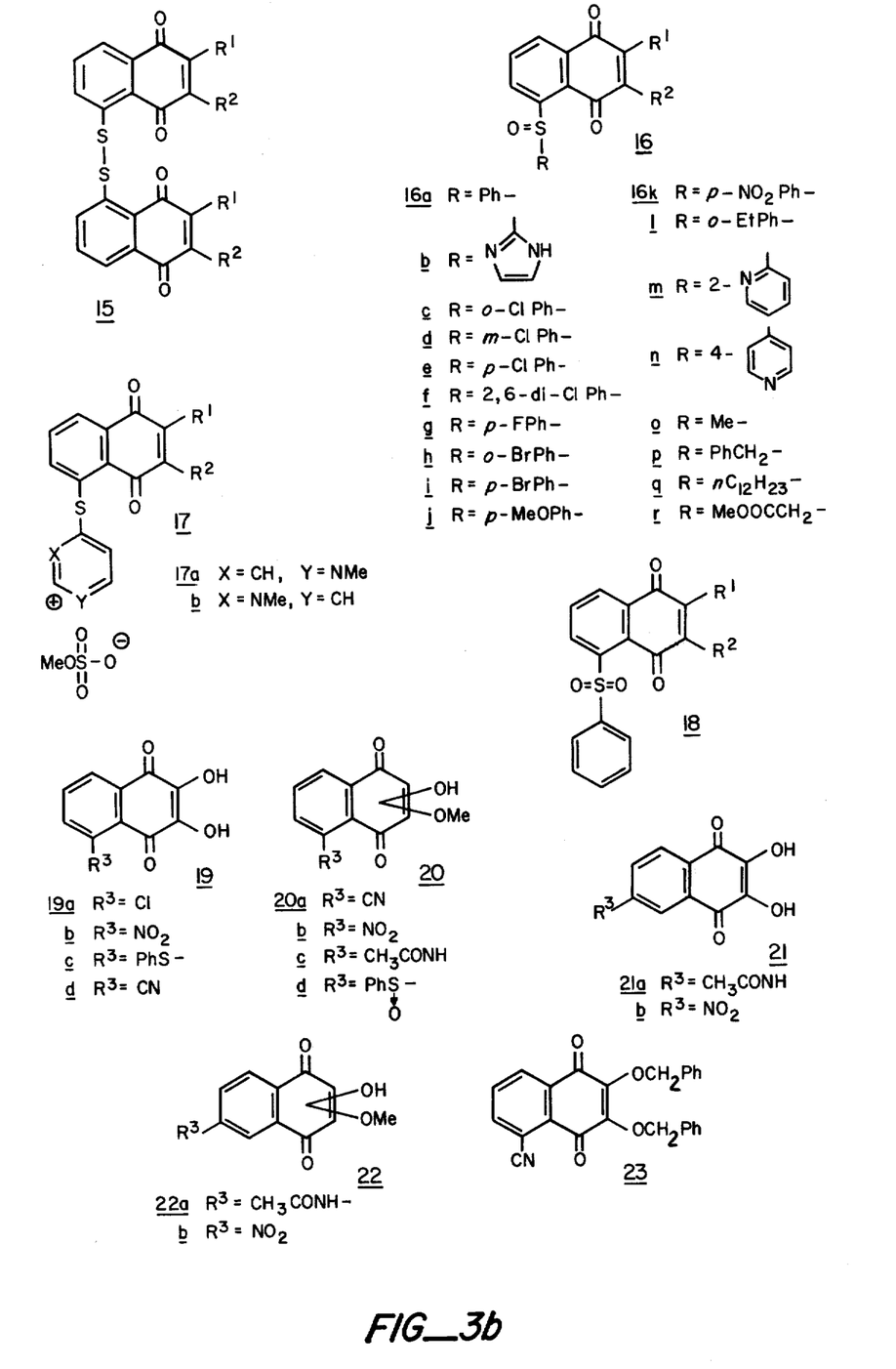

The preferred procedure for the preparation of the compounds of the present invention where $R^3$ is $C_1$ to $C_6$ linear or branched alkylthio, the compound 12a, FIG. 3a is first converted to the di(2,3-$R^1$, $R^2$-1,4-naphthoquinone)-5-disulfide, FIG. 3b, compound 15. A mixture of an alkaline earth or alkali metal thiol carboxylate such as the acetate, propionate, butyrate and the like (compounds of the formula where y is the integer 0 to 18, M is an alkali or alkaline earth metal and x is the valence of said metal) in an inert organic solvent is added to a solution or dispersion of compound 12a at a temperature of −10° to +10° C. over a period of about 1 to about 120 minutes preferably 5 to 30 minutes. Reaction media include a variety of polar inert solvents such as dimethylformamide, dimethylsulfoxide and the like. After further reaction, typically for about 1 to about 10 hours at 20° to 50°, the disulfide is isolated. This compound can then be used to prepare the alkyl or aralkyl sulfides (FIG. 3a, compound 14q-14t) by first treating it with a mixture of sodium borohydride in an inert organic solvent and adding to such mixture at a temperature of about −10° to about 75° for 1 to 10 hours an appropriate alkylating agent such as a dialkyl sulfate, an alkyl halide, an aralkyl halide and the like. Illustrative of such alkylating agents are the compounds methyl bromide, methyl iodide, dimethyl sulfate and benzyl bromide. Preferably alkyl iodide is used as the alkylating agent herein.

The 5-$C_6$ to $C_{10}$ carbocyclic aryl sulfinylnaphthoquinones of the present invention (FIG. 3b, compound(s) 16 are prepared from the compounds 14c-u of the present invention by oxidation with a suitable peracid in an inert organic solvent. Preferably, the compound(s) 16, FIG. 3b are prepared from the corresponding compounds 14c-u by admixture with peracetic acid in an inert organic solvent.

Where appropriate, salts of the compounds bearing heterocyclic aryl substituents are prepared. For example, the methylsulfate salt of the 5-(pyridin-4-yl)-1,4-naphthoquinone is readily prepared by admixture with dimethylsulfate in an inert organic solvent such as tetrahydrofuran. Salt formations of this type are well known in the prior art.

The compounds of the present invention bearing a 5-sulfonyl substituent are prepared by further oxidizing the compounds 14c-u with a suitable peracid typically at −10° to 75° for 1 to 10 hours. Preferably, m-chloroperbenzoic acid in an inert organic solvent with the compounds 14c-u at room temperature affords the desired sulfonyl compounds.

The above preparations are generally carried out starting with various 5- or 6-substituted-2,3-dialkoxy-1,4-naphthoquinones, i.e., the compounds of formula (I) where $R^1 = R^2 = C_1$ to $C_{18}$ linear or branched alkoxy. These alkoxide groups are readily hydrolyzed to yield the 2-, the 3-, or the 2,3-hydroxides (FIG. 3b, compounds 19, 20 and 21). The reaction is preferably carried out at −10° to 70° for 1 to 10 hours in an inert organic solvent such as methylene chloride having added thereto a freshly distilled solution of boron trichloride. Rather than removing the alkoxides to yield the respective hydroxy compounds, it is further provided in the process of the present invention to directly convert the aliphatic alkoxides to aryl-substituted alkoxides (FIG. 3b compounds 23) by a simple interchange reaction. In this case the compounds of the present invention bearing a 2,3-substituted $C_1$ to $C_{18}$ linear or branched alkoxide are admixed with a suitable inert organic solvent and added thereto is the desired aryl-substituted aliphatic alcohol. An alkali metal hydride such as sodium hydride is added to the solution and the mixture stirred typically at room temperature. The compounds of the present invention, bearing the aryl-substituted alkyl group readily form and can be isolated from the reaction mass by conventional methods (column chromatography, etc.).

In the present specification and claims the term "$C_1$ to $C_{18}$ linear or branched alkyl" is intended to mean alkyl groups containing 1 to 18 carbon atoms including straight chain groups, branched chain groups and straight or branched chain groups optionally having an optionally substitued phenyl group (sometimes referred to herein as aralkyl). Illustrative of such groups are for example, methyl, ethyl, n-propyl, isopropyl, n-hexyl, 2-methylpentyl, n-octyl, benzyl, 4-methylbenzyl, 4-chlorobenzyl and the like.

The term "$C_2$ to $C_7$ linear or branched acyl" refers to those 2 to 7 carbon chains including the phenyl group and bearing the group C=O. Similarly "$C_2$ to $C_7$ acyloxy" refers to the 2 to 7 carbon chain, including the phenyl and bearing the group —C(O)O—. The term "$C_1$ to $C_{18}$ linear or branched alkoxy" is intended to mean the straight or branched aliphatic compounds of 1 to 18 carbon atoms and optionally containing an optionally substituted phenyl group having bonded thereto an oxygen moiety. These alkoxides include the methoxide, ethoxide, n-propoxide, n-butoxide, n-pentoxide, n-hexoxide, isopropoxide and the like.

As used in the specification and claims herein, the term "heterocyclic aryl" is defined as those cyclic aromatic compounds having 3 to 9 ring carbon atoms and having at least one and up to two heteroatoms in the ring selected from the group nitrogen, oxygen and sulfur with or without substituents thereon, the substituents being halo, $C_1$ to $C_4$ linear or branched alkyl (as defined above), cyano, $C_1$ to $C_4$ linear or branched alkoxy (as defined above). Examples of such include the groups phenylthio, benzophenylthio, furyl, 2H-pyryl, pyrroyl, imidazolyl, pyrazolyl, pyridinyl, pyrimidinyl, indolyl, quinolinyl, indozolyl and the like.

By the term "pharmaceutically acceptable salts" as used in the case of the various $R^3$ heterocyclic aryl substituents herein is intended to mean those non-toxic pharmaceutically acceptable hydrogen-anion addition salts which do not adversely affect the pharmaceutical properties of the parent compounds. With respect to these addition salts, suitable inorganic anions include, for example, chloride, bromide, iodide, sulfate, phosphate, nitrate and the like. Suitable organic anions include, for example, acetate, benzoate, lactate, picrate, propionate, butyrate, valerate, tartrate, maleate, fumarate, citrate, succinate, tosylate, ascorbate, nicotinate, adipate, gluconate and the like.

The following specific description is given to enable those skilled in the art to more clearly understand and practice the present invention. It should not be considered as a limitation upon the scope of the invention but merely as illustrative and representative thereof.

All temperatures in this specification are in degrees Centigrade unless otherwise noted.

Figure 2:
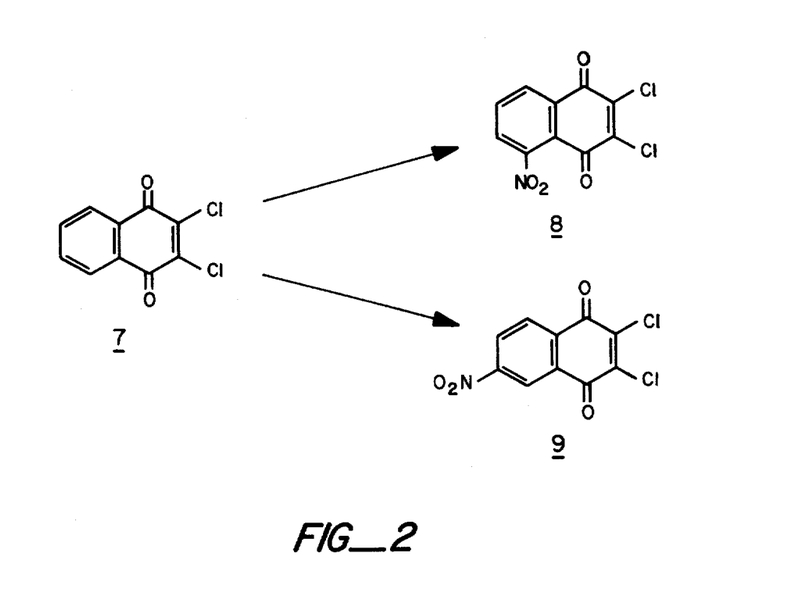
FIG. 2 is the reaction sequence for the preparation of the chemical intermediates used to prepare the compounds of the present invention.

For Preparations 1 and 2 and Examples 1 and 2, reference should be made to FIG. 1. Example 3 is represented by FIG. 2. The remaining Examples refer to compounds represented in FIGS. 3a and 3b.

PREPARATION 1

4-Chloro-alpha,alpha,alpha',alpha'-tetrabromo-o-xylene.

A mixture of 4-chloro-o-xylene (1, $R^3$ = Cl, 14.0 g, 0.1 mol) and freshly recrystallized N-bromosuccinimide (80 g, 0.45 mol) in carbon tetrachloride (1 L) is irradiated for 2½ hours (hr) with a 250 watt tungsten infrared lamp positioned so that the solvent refluxed gently. The solid material is then removed by filtration, the filtrate is concentrated in vacuo and the crystalline residue is recrystallized from isopropanol giving 34 g (75%) of 2, $R^3$=Cl with mp 108°–111° [Bull. Soc. Chim., 2966 (1966), mp 114°].

In a similar fashion, the following compounds are prepared:

4-fluoro-alpha,alpha,alpha',alpha'-tetrabromo-o-xylene, mp 87°–91°;

4-bromo-alpha,alpha,alpha',alpha'-tetrabromo-o-xylene, mp 102°–105° (lit. 116°);

4-methoxy-alpha,alpha,alpha',alpha'-tetrabromo-o-xylene,. bp 160° (bath temp.), 0.1 mm;

4-nitro-alpha,alpha,alpha',alpha'-tetrabromo-o-xylene, mp 120°–121°;

4-cyano-alpha,alpha,alpha',alpha'-tetrabromo-o-xylene, mp 114°–115°;

4-acetoxy-alpha,alpha,alpha',alpha'-tetrabromo-o-xylene, mp 103°–104°; and 2,3-di(dibromomethyl)naphthalene, mp 156°–160°.

PREPARATION 2

4-Chloro-1,2-phthalaldehyde

A mixture of 2, $R^3$=Cl (22.8 g, 0.05 mol), silver acetate (36.6 g, 0.22 mol) and glacial acetic acid (500 ml) is heated under reflux for 1½ hr. The silver salts are filtered off, washed with chloroform and the combined filtrates concentrated to dryness in vacuo. The last traces of acetic acid are removed from the residue by evaporation with toluene. The resultant semicrystalline material 3, $R^3$=Cl is dissolved in dioxane (500 ml) and a solution of sodium carbonate (53 g) in water (500 ml) is added. This mixture is shaken vigorously at 22° for 20 minutes, saturated with sodium chloride and then extracted with ethyl acetate (2×500 ml). The combined organic extracts are washed with brine (2×400 ml), dried with MgSO$_4$ and concentrated in vacuo giving 6.0 g (72%) of almost pure 4-chloro-1,2-phthalaldehyde (4b). Sublimation at 75° and 0.05 mm Hg affords 5.4 g of 4, $R^3$=Cl with mp 72°–76°.

In a similar manner, the following compounds are prepared:

4-fluoro-1,2-phthalaldehyde, mp 37°–40;
4-bromo-1,2-phthalaldehyde, mp 87°–94°;
4-methoxy-1,2-phthalaldehyde, mp 44°–45°;
4-nitro-1,2-phthalaldehyde, foam;
4-cyano-1,2-phthalaldehyde, mp 127°–128°; and
2,3-naphthodialdehyde, mp 127°–131°.

EXAMPLE 1

6-Chloro-iso-naphthazarin

A solution of sodium carbonate (12.3 g) in water (290 ml) is added to a vigorously stirred solution of 4-chloro-1,2-phthalaldehyde (4.88 g, 29 mmol) in an oxygen atmosphere followed immediately by the addition, over a five minute period, of a solution of glyoxal bisulfite (16.4 g, 58 mmol) and potassium cyanide (1.88 g, 29 mmol) in water (290 ml). The reaction mixture is stirred in the oxygen atmosphere for a further 5 minutes. It is then treated with 6 N hydrochloric acid (50 ml), cooled in an ice-salt bath and further diluted with water (500 ml). The crystalline product is collected by filtration, washed with water, dried and recrystallized from water:methanol (2:1) giving 3.56 g (55%) of 6-chloro-iso-naphthazarin, mp 228°–229°.

Anal. Calcd. for $C_{10}H_5ClO_4$ (224.60): C, 53.48; H, 2.24. Found: C, 53.50; H, 2.30.

In a similar manner the following compounds are prepared:

6-fluoro-iso-naphthazarin, mp 217°–218°;
6-chloro-iso-naphthazarin, mp 240°–241° [lit., Berichte, 80, 391, 397 (1947), mp 240°–241°];
6-methoxy-iso-naphthazarin, mp 224°–225°;
6-cyano-iso-naphthazone, mp 315°–320°; and
6,7-benzo-iso-naphthazarin, mp 335°–337°.

EXAMPLE 2

6-Chloro-oxalin

Chlorine gas is passed through a stirred suspension of 6-chloro-iso-naphthazarin (225 mg. 1 mmol) in 50% acetic acid (2 ml) until a pale yellow clear solution is obtained. Excess chlorine is then removed by a nitrogen stream. The resulting solution is concentrated to dryness in vacuo and the residue recrystallized from acetonitrile:benzene (1:2) giving 214 mg (83%) of 6-chloro-oxalin as a white crystalline solid with mp 134°–136°.

In a similar manner, the following compounds are prepared:

6-fluoro-oxalin, mp 131°–132°;
6-bromo-oxalin, mp 147°–148°; and
6-methoxy-oxalin, mp 130°–131°

EXAMPLE 3

2,3-Dichloro-5 and 6-nitro-1,4-naphthoquinone

Finely powdered 2,3-dichloro-1,4-naphthoquinone (7, 50 g. 0.22 mol) is added to a stired mixture of concentrated sulfuric acid (170 ml) and 90% nitric acid (102 ml) at a rate so that the exothermic reaction raises the temperature to 60°. The resulting mixture is stirred at 60° for a further 2 hours. The yellow crystalline solid is filtered off, washed thoroughly with water and recrystallized from chloroform giving 22.9 g (37%) of the 5-nitro isomer (8) with mp 156°–157°. The above strongly acidic filtrate is poured onto ice water. The resultant solid is filtered off, washed thoroughly with water and dried giving 20.8 g of a mixture of 8 and 9. Fractional crystallization of this mixture from acetic acid and chloroform:iso-propanol affords 2.8 g (4.7%) of the 6-nitro isomer 9 with mp 184°–187°.

Further quantities of both 8 and 9 are obtained from the recrystallization mother liquors by chromatography on a silica gel column eluting with chloroform:cyclohexane mixtures.

EXAMPLE 4

2,3-Dimethoxy-5-nitro-1,4-naphthoquinone

A solution of 2,3-dichloro-5-nitro-1,4-naphthoquinone (8, 2.72 g, 10 mmol) in anhydrous tetrahydrofuran (15 ml) is added to a solution of 1 N sodium methoxide (25 ml, 25 mmol) and the resulting solution stored at 22° for 16 hours. Acetic acid (1 ml) is then added, the solution concentrated in vacuo and the residue partitioned between water (50 ml) and chloroform (100 ml). The aqueous phase is further extracted with chloroform (2×50 ml). The combined chloroform extracts are dried with MgSO$_4$ and concentrated in vacuo. The residue is recrystallized from methanol giving 1.99 g (76%) of 10 FIG. 3a ($R^1$=$R^2$=OCH$_3$) with mp 156°–157°.

In the same fashion the following compounds are prepared:

2,3-dimethoxy-6-nitro-1,4-naphthoquinone, mp 113°–114°; and 2,3-dibenzyloxy-5-nitro-1,4-naphthoquinone, mp 116°–117° (from sodium benzyloxide).

EXAMPLE 5

2,3-Dimethoxy-5-amino-1,4-naphthoquinone

Hydrazine (4.0 ml, 125 mmol of 97%) is added dropwise, over a 2 hour period, to a stirred mixture of the captioned compound of Example 4 (19.9 g, 75.6 mmol), 5% palladium on carbon (10 g) and ethanol (750 ml) in a nitrogen atmosphere. The catalyst is filtered off through a celite pad that was washed with hot ethanol (2×300 ml). The combined filtrate and washings are concentrated to dryness in vacuo and the residue recrystallized from water:ethanol (1.5:1) giving 14.6 g (83%) of 12a, $R^1 = R^2 = OCH_3$, with mp 116°–117°.

Similarly, 2,3-dimethoxy-6-amino-1,4-naphthoquinone, 13a $R^1 = R^2 = OCH_3$, mp 196°–197° C., is prepared.

EXAMPLE 6

2,3-dimethoxy-5-acetamido-1,4-naphthoquinone

Acetyl chloride (1.5 ml, 20 mmol) is added dropwise, over 10 min, to an ice water cooled, stirred suspension of 12a from Example 5 (466 mg, 2 mmol) in chloroform (15 ml) containing pyridine (1.6 ml, 20 mmol). After a total reaction time of 30 min, the mixture is diluted with chloroform (50 ml) and then washed with water (2×25 ml). The chloroform phase is dried over $MgSO_4$, concentrated to dryness and the residue recrystallized from iso-propanol affording 498 mg (85%) of 12b $R^1 = R^2 = OCH_3$, with mp 162°–163°.

EXAMPLE 7

6-Acetamido-2,3-dimethoxy-1,4-naphthoquinone

A suspension of 13a, Example 6 (50 mg, 0.21 mmol), acetic anhydride (0.5 ml) and 4-dimethylaminopyridine (about 5 mg) in chloroform (1 ml) containing pyridine (0.5 ml) is stirred at 22° for two hours. The light orange solid is removed by filtration, washed with chloroform and recrystallized from glacial acetic acid giving 27.5 mg (45%) of 13b, $R^1 = R^2 = OCH_3$, with mp 226°–228°.

EXAMPLE 8

2,3-Dimethoxy-5-chloro-1,4-naphthoquinone

A solution of sodium nitrite (0.69 g, 10 mmol) in water (5 ml) is added at 0°–5° to a solution of 12a (1.17 g, 5 mmol) in 5:1 acetic acid:water (25 ml) containing concentrated hydrochloric acid (1.7 ml). A further quantity of sodium nitrite (0.69 g) is then added to the reaction mixture after cooling to −5°, followed by a solution of cuprous chloride (0.6 g) in concentrated hydrochloric acid (5 ml). The mixture is allowed to warm to 22° and solid cuprous chloride is added portionwise until the mixture assumes a green color. Water is then added to the reaction mixture and the precipitated yellow solid filtered off, washed with water and recrystallized from methanol:water (2:1) giving 1.01 of 14a $R^1 = R^2 = OCH_3$, with mp 120°–121°.

EXAMPLE 9

2,3-Dimethoxy-5-cyano-1,4-naphthoquinone

A solution of sodium nitrite (2.21 g, 32 mmol) in water (6 ml) is added at 0°–5° to a stirred suspension of 12a (3.73 g, 16 mmol) in 3:1 water:tetrahydrofuran (20 ml) containing concentrated hydrochloric acid (6.7 ml) and the resulting mixture is stirred at 0°–5° for a further 1¼ hour. The almost clear solution is then neutralized with sodium carbonate, filtered and added at 5° to a vigorously stirred solution of cuprous chloride (4.75 g) and sodium cyanide (5.88 g) in water (80 ml). Ethyl acetate (100 ml) is added and the mixture is heated at 45° for 0.5 hours, filtered through a celite bed and separated into the two phases. The aqueous phase is extracted with ethyl acetate (2×100 ml). The combined organic phases are extracted with brine (150 ml), dried over $MgSO_4$ and concentrated to dryness in vacuo. The residue is recrystallized from isopropanol giving 2.96 g (76%) of 14b, $R^1 = R^2 = OCH_3$, with mp 171°–172°.

EXAMPLE 10

2,3-Dimethoxy-5-phenylthio-1,4-naphthoquinone

Method A. Sodium nitrite (0.18 g) is added at 0°–5° to a stirred suspension of 12a (233 mg, 1 mmol) in 0.6 N hydrochloric acid (10 ml) and tetrahydrofuran (1 ml). The mixture is stirred at 5° for 10 minutes until a clear solution is obtained and is then neutralized by the addition of sodium carbonate. The ice cold solution is then slowly added to a vigorously stirred two-phase mixture in a nitrogen atmosphere at 50° composed of potassium hydroxide (0.16 g), water (10 ml), thiophenol (0.32 ml) and ethyl acetate (35 ml). After a total reaction time of 20 min, the mixture is partitioned between ethyl acetate (40 ml) and brine (100 ml). The ethyl acetate phase is dried over $MgSO_4$ and concentrated in vacuo. The residue is purified by chromatography on a thick layer silica gel plate using acetone:toluene:chloroform (1:20:20) giving a solid that, after recrystallizing from isopropanol, affords 70 mg (21%) of 14c, $R^1 = R^2 = OCH_3$, with mp 76°–77°.

Similarly, using imidazolyl-2-thiol in place of thiophenol, 2,3-dimethoxy-5-(imidazol-2-yl)thiol-1,4-naphthoquinone, 14d, $R^1 = R^2 = OCH_3$, mp 97°–100° C., is prepared.

Method B. Thiophenol (6.0 ml, 59 mmol) is added at −30° to a stirred mixture of 100% sodium hydride (1.4 g, 59 mmol) and dimethylformamide (200 ml) and the resulting mixture is stirred at 22° for 16 hours. This mixture is then cooled to −50° and a solution of 10 $R^1 = R^2 = OCH_3$, (13.0 g, 49 mmol) in dimethylformamide (100 ml) is added over 30 min. The resulting mixture is allowed to warm to 22° over 1 hour before cooled to −50° and neutralized with acetic acid (5.4 ml, 90 mmol). The reaction mixture is then poured into a mixture of water (1.8 L) and methanol (700 mL). The precipitated material is filtered off and recrystallized from methanol giving 10.3 g (64%) of 14c $R^1 = R^2 = OCH_3$, with mp 76°–79°. A further amount (2.2 g, 14%) mp 76°–77° is obtained in a second crop from the recrystallization.

Similarly, by substitution of ther aromatic thiols for thiophenol, $R^1 = R^2 = OCH_3$, the following compounds are prepared:

2,3-dimethoxy-5-(2-chlorophenylthio)-1,4-naphthoquinone, 14e, mp 139°–140°;

2,3-dimethoxy-5-(3-chlorophenylthio)-1,4-naphthoquinone, 14f, mp 125°–126°;

2,3-dimethoxy-5-(4-chlorophenylthio)-1,4-naphthoquinone, 14g, mp 138°–139°;

2,3-dimethoxy-5-(2,6-dichlorophenylthio)-1,4-naphthoquinone, 14h, mp 158°–159°.

2,3-dimethoxy-5-(4-fluorophenylthio)-1,4-naphthoquinone, 14i, mp 124°–125°;

2,3-dimethoxy-5-(2-bromophenylthio)-1,4-naphthoquinone, 14j, mp 152°–153°;

2,3-dimethoxy-5-(4-bromophenylthio)-1,4-naphthoquinone, 14k, mp 142°–143°;

2,3-dimethoxy-5-(4-methoxyphenylthio)-1,4-naphthoquinone, 14l, mp 104°–105°;

2,3-dimethoxy-5-(4-nitrophenylthio)-1,4-naphthoquinone, 14m, mp 213°–214°;

2,3-dimethoxy-5-(ethylphenylthio)-1,4-naphthoquinone, 14n, mp 114°–116°;

2,3-dimethoxy-5-pyridin-2-ylthio-1,4-naphthoquinone, 14o, mp 110°–111°;

2,3-dimethoxy-5-pyridin-4-ylthio-1,4-naphthoquinone, 14p, mp 158°–159°; and 2,3-dimethoxy-5-(acetanilide-4-thio)-1,4-naphthoquinone, 14q, mp 118°–127°.

EXAMPLE 11

Di-(2,3-dimethoxy-1,4-naphthoquinone-5)disulfide

A slurry of potassium thiolacetate (1.5 g, 13.1 mmol) in dimethylformamide (25 ml) is added over 10 minutes to a solution at 0°–5° of 12a from Example 5 (2.63 g, 10 mmol) in dimethylformamide (25 ml). The mixture is allowed to warm to 22° and, after 2 hours, an additional quantity of potassium thiolacetate (1.25 g) is added. After a further 45 minute reaction, the mixture is added to ice water (500 ml) that was adjusted to pH 6 with acetic acid. The precipitated solid is filtered off, washed with water and recrystallized from chloroform:methanol (1:1) giving 1.32 g. (53%) of 15 $R^1 = R^2 = OCH_3$, with mp 220°–221°.

EXAMPLE 12

2,3-Dimethoxy-5-methylthio-1,4-naphthoquinone

Sodium borohydride (100 mg) is added portionwise to a stirred suspension of 15 (0.5 g, 1 mmol) in 7:1 tetrahydrofuran:iso-propanol (40 ml) in a nitrogen atmosphere until TLC analysis indicates that no starting material remains. Methyl iodide (0.2 ml) is then added and, after 5 minutes, the reaction mixture is poured into ice water (300 ml). 10% Ferric chloride (10 ml) is subsequently added. The precipitated solid is filtered off, washed with water and recrystallized from isopropanol giving 0.36 g (68%) of 14q $R^1 = R^2 = OCH_3$, with mp 112°–113°.

By substituting other alkyl iodides for methyl iodide the following are prepared; $R^1 = R^2 = OCH_3$:

2,3-dimethoxy-5-benzylthio-1,4-naphthoquinone, 14r, m.p. 142°–143°;

2,3-dimethoxy-5-n-dodecylthio-1,4-naphthoquinone, 14s, m.p. 88°–89°;

2,3-dimethoxy-5-carbomethoxymethylthio-1,4-naphthoquinone, 14t, m.p. 119°–120°.

EXAMPLE 13

2,3-Dimethoxy-5-phenylsulfinyl-1,4-naphthoquinone

Forty percent (w/v) peracetic acid in acetic acid (1 ml) is added over 30 minutes to a solution of 14c (0.98 g, 3 mmol) in methylene chloride (15 ml). Excess peracetic acid is destroyed by the addition of a few milligrams of 5% palladium on carbon and the mixture filtered through a celite bed. The filtrate is concentrated in vacuo and the residue recrystallized from methanol giving 0.59 g (58%) of 16a, $R^1 = R^2 = OCH_3$, with mp 169°–170° and a second crop of 0.14 g (14%) with mp 165°–167°.

Similarly, using either peracetic acid or m-chloroperbenzoic acid, the following compounds are prepared from the respective compounds 14 where $R^1 = R^2 = OCH_3$:

2,3-dimethoxy-5-(imidazol-2-yl)sulfinyl-1,4-naphthoquinone, 16b;

2,3-dimethoxy-5-(2-chlorophenyl)sulfinyl-1,4-naphthoquinone, 16c, mp 193°–194°;

2,3-dimethoxy-5-(3-chlorophenyl)sulfinyl-1,4-naphthoquinone, 16d, mp 150°–151°;

2,3-dimethoxy-5-(4-chlorophenyl)sulfinyl-1,4-naphthoquinone, 16e, mp 191°–192°;

2,3-dimethoxy-5-(2,6-dichlorophenyl)sulfinyl-1,4-naphthoquinone, 16f, mp 210°–211°;

2,3-dimethoxy-5-(4-fluorophenyl)sulfinyl-1,4-naphthoquinone, 16g, mp 133°–134°;

2,3-dimethoxy-5-(2-bromophenyl)sulfinyl-1,4-naphthoquinone, 16h, mp 199°–200°;

2,3-dimethoxy-5-(4-bromophenyl)sulfinyl-1,4-naphthoquinone, 16i, mp 144°–145°;

2,3-dimethoxy-5-(4-methoxyphenyl)sulfinyl-1,4-naphthoquinone, 16j, mp 110°–111°;

2,3-dimethoxy-5-(4-nitrophenyl)sulfinyl-1,4-naphthoquinone, 16k, mp 193°–194°;

2,3-dimethoxy-5-(2-ethylphenyl)sulfinyl-1,4-naphthoquinone, 16l, mp 166°–167°;

2,3-dimethoxy-5-(pyrimidin-2-yl)sulfinyl-1,4-naphthoquinone, 16m, mp 185°–186°;

2,3-dimethoxy-5-(pyrimidin-4-yl)sulfinyl-1,4-naphthoquinone, 16n, mp 102°–103°;

2,3-dimethoxy-5-methylsulfinyl-1,4-naphthoquinone, 16o, mp 102°–105°;

2,3-dimethoxy-5-benzylsulfinyl-1,4-naphthoquinone, 16p, mp 160°–161°;

2,3-dimethoxy-5-n-dodecylsulfinyl-1,4-naphthoquinone, 16q, mp 88°–89°; and 2,3-dimethoxy-5-carbomethoxymethylsulfinyl-1,4-naphthoquinone, 16r, mp 158°–159°.

EXAMPLE 14

2,3-Dimethoxy-5-(4-methylpyridiniumthio)-1,4-naphthoquinone methyl sulfate

A mixture of dimethylsulfate (0.19 ml, 2 mmol) and 14p (327 mg, 1 mmol) in tetrahydrofuran (10 ml) is heated under reflux for 3 hours and then cooled to 20°. The orange solid is filtered off, washed with tetrahydrofuran and recrystallized from ethanol:isopropanol giving 279 mg of 17a $R^1 = R^2 = OCH_3$, (62%, mp 160°–162° and a second crop of 110 mg (24%).

Similarly, the 2-pyridylthio compound 14o is converted to the N-methyl derivative 17b, $R^1 = R^2 = OCH_3$.

Similarly, 17a and 17b are converted to the corresponding sulfoxides as described above (mp 175°–176°.

EXAMPLE 15

2,3-Dimethoxy-5-phenylsulfonyl-1,4-naphthoquinone

A mixture of m-chloroperbenzoic acid (300 mg) and 14c (200 mg, 0.61 mmol) in methylene chloride (5 ml) is stirred at 22° for 16 hours and the resulting solution then passed through an alumina column (10 g of Activity 1) eluting with chloroform. The eluates are concentrated to dryness and the residue is crystallized from isopropanol giving 95 mg (43%) of 18, $R^1 = R^2 = OCH_3$, mp 141°–142°.

EXAMPLE 16

5-Phenylthio-iso-naphthazarin

A solution of 14c (3 g, 9.2 mmol) in methylene chloride is added dropwise over 20 minutes at −65° to a stirred solution of freshly distilled boron trichloride (10 ml) in methylene (100 ml). After a further 5 minute reaction, 1:1 chloroform:methanol (20 ml) is added and the resulting solution is concentrated to dryness in vacuo. The residue is recrystallized from 2:1 methanol:-water (150 ml) and then isopropanol giving 2.0 g (75% of 19c, mp 228°-230°.

A similar treatment of 14a where $R^1=R^2=OCH_3$ gives 5-chloro-iso-naphthazarin, 19a, mp 240°-245°.

A similar treatment of 14b where $R^1=R^2=OCH_3$ gives the monomethoxy compound 2- or 3-hydroxy-2- or 3-methoxy-5-cyano-1,4-naphthoquinone, 20a, with mp 237°-242°.

A similar treatment on 10a where $R^1=R^2=OCH_3$ gives 2- or 3-hydroxy-2- or 3-methoxy-5-nitro-1,4-naphthoquinone, 20b with mp 191°-192°.

A similar treatment of 10b where $R^1=R^2=OCH_3$ gives 2,3-dihydroxy-5-nitro-1,4-naphthoquinone, 19b with mp 232°-238°.

A similar treatment of 12b where $R^1=R^2=OCH_3$ gives 2- or 3-dihydroxy-2- or 3-methoxy-5-acetamido-1,4-naphthoquinone, 20c with mp 242°-248°.

A similar treatment of 16a where $R^1=R^2=OCH_3$ gives 2- or 3-hydroxy-2- or 3-methoxy-5-phenylsulfinyl-1,4-naphthoquinone, 20d with mp 215°-220°.

A similar treatment of 13b where $R^1=R^2=OCH_3$ gives 2,3-dihydroxy-6-acetamido-1,4-naphthoquinone, 21a.

A similar treatment of 11 where $R^1=R^2=OCH_3$ gives 2- or 3-methoxy-6-nitro-1,4-naphthoquinone, 22b with mp 239°-240°.

EXAMPLE 17

2,3-Dibenzyloxy-5-cyano-1,4-naphthoquinone

14b From Example 9 (972 mg, 4 mmol) is dissolved in tetrahydrofuran (100 ml) containing benzyl alcohol (8 ml) and the tetrahydrofuran (40 ml) is distilled off. The remaining solution is cooled to 15° and sodium hydride (5 mg) with 3 Å molecular sieve (2 g) is added. The resulting mixture is stirred at 15°-20° for 20 minutes. The mixture is filtered through a celite bed, the filtrate concentrated to dryness and the residue crystallized from isopropanol giving 1.01 g (64%) of 23 with mp 118°-121°.

Treatment of 23 with boron trichloride as in Example 16 above gives 2,3-dihydroxy-5-cyano-1,4-naphthoquinone, 19d with mp 305°-312°.

Since known effective anti-psoriasis agents inhibit epidermal cell proliferation, an animal assay using young male rats has been developed wherein the test agent in an appropriate carrier is applied to the skin of one flank of the test animal while the carrier is applied to the other i.e., the control. At a suitable time interval after one or more applications of the composition, the skin is removed from the animal and skin plugs taken from both the treated and the control areas are incubated in vitro with tritium labelled thymidine (a precursor of DNA synthesis). A comparative measure of the amount of radio-labelled thymidine incorporated into the DNA of plugs from the treated and control flanks gives a measure of the degree of inhibition of DNA synthesis and hence epidermal proliferation which has occurred in response to the treatment.

Compositions illustrative of the compositions of the present invention are tested in the rat in the method disclosed above. The tests are specifically carried out as follows:

Male albino rats, 21-22 days old are shaved on the back and both flanks with electric clippers twenty-four hours prior to testing. Test agents were dissolved in ethanol, acetone, dimethyl sulfoxide or a mixture of these solvents. Solutions (0.10 ml) containing the test agent, are applied to the right flank of the animals and the carrier alone (0.10 ml) is applied to the left flank. The area covered is approximately 10 sq. cm. Applications are made at 9:00 a.m. and 4:00 p.m. on days 1, 2 and 3. On day 4 the animals are sacrificed by carbon dioxide asphyxiation, and the full thickness skin from the back and both flanks are removed. Subcutaneous fat and muscle are scraped away and plugs consisting of epidermis and dermis, 6 mm. in diameter are punched out, five from the control flank and five from the treated flank. These are incubated at 37° individually floating on 3 ml of Dulbecco's Modified Eagle Medium containing tritiated thymidine (10 microcuries/milliliter). After two hours incubation the plugs are frozen, thawed, blotted dry, rinsed 3 times in 30% aqueous acetic acid and once in absolute ethanol to remove unincorporated tritiated thymidine. The washed plugs are digested in NCS solubilizer for liquid scintillation counting in order to determine the amount of tritiated thymidine incorporated into the DNA. The inhibitory effect of the treatment is determined by comparing the amount of radioactivity incorporated into plugs from the treated side with that incorporated into plugs from the control flank. For each test at least two animals are used. The data are recorded for each animal as the ratio of mean radioactivity in the treated side to the mean radioactivity of the control side (×100).

| $R^1$ | $R^2$ | $R^3$ | % CONCENTRATION, SOLVENT (RATIOS)[1] | EFFECTIVENESS[2] |
|---|---|---|---|---|
| OH | OH | H | 2.0% DMSO/EtOH (1/1) | 55, 52 |
|  |  |  | 1.0% EtOH/Acetone (1/1) | 59, 64 |
|  |  |  | 2.5% EtOH/Acetone/DMSO (4.5/4.5/1) | 50, 83 |
|  |  |  | 1.7% DMSO/Acetone (1/2) | 75, 84 |
|  |  |  | 2.0% DMSO/Acetone/EtOH (2/4/4) | 82, 95 |
| OH | OH | $OCH_3$ | 1.0% Ethanol/Acetone (1/1) | 59, 90 |
|  |  |  | 2.0% DMSO/Acetone/EtOH (1/4.5/4.5) | 58, 93 |
|  |  |  | 2.0% DMSO/EtOH/Acetone (1/1/1) | 47, 50 |
| OH | OH | Br | 2.0% DMSO/EtOH/Acetone (2/4/4) | 58, 62 |
| OH | OH | Cl | 2% DMSO/EtOH (1/1) | 69, 56 |
|  |  |  | 2% DMSO/EtOH/Acetone (1/4.5/4.5) | 85, 82 |
| OH | OH | F | 2% DMSO/EtOH/Acetone (1/4.5/4.5) | 76, 64 |

[1] DMSO - dimethylsulfoxide
EtOH - ethyl alcohol

[2] $\frac{\text{Mean Radioactivity treated Side}}{\text{Mean Radioactivity Control}} \times 100$ The amount of tritiated thymidine incorporated is primarily due to epidermal cells, and hence the amount of radioactivity in these tests is directly related to the number of cells (epidermal) engaged in proliferation (DNA synthesis) at the moment of sacrifice. As noted earlier, epidermal cell hyper-proliferation is symptomatic of psoriasis. The compounds exemplified showed inhibitory activity against epidermal cell proliferation and as a result are anti-psoriatic agents.

What is claimed is:

1. A method for relieving the condition of psoriasis which comprises topically administering to mammals in need thereof an amount of a compound of the formula (I)

where $R^1$ and $R^2$ are the same or different and are hydrogen, hydroxy or $C_1$ to $C_{18}$ linear or branched alkoxy and $R^3$ is hydrogen, halo, cyano or $C_1$ to $C_{18}$ linear or branched alkoxy, with the proviso that $R^1$ and $R^2$ are not both hydrogen, sufficient to relieve the condition of psoriasis in mammals in combination with a pharmaceutically acceptable, non-toxic carrier suitable for said administration form.

2. The method according to claim 1 wherein said compound is (I)

3. The method according to claim 2 wherein $R^1$ and $R^2$ are hydroxy and $R^3$ is selected from the group halo, cyano, and $C_1$ to $C_4$ alkoxy.

4. The method according to claim 2 wherein $R^1$ is $C_1$ to $C_4$ linear or branched alkoxy and $R^2$ and $R^3$ are hydrogen.

5. The method according to claim 3 where $R^3$ is selected from the group fluoro, chloro and bromo.

6. The method according to claim 3 wherein $R^3$ is cyano.

7. The method according to claim 2 wherein the compound of formula (I) is 2,3-dihydroxy-6-bromo-1,4-naphthoquinone.

8. The method of claim 1 wherein said compound is 6-chloro-2,3-dihydroxy-1,4-naphthoquinone.

* * * * *